United States Patent [19]

Poindexter

[11] Patent Number: 4,994,476

[45] Date of Patent: Feb. 19, 1991

[54] DIHYDROPYRIDIN-3,5-DICARBOXYLATES INCORPORATING ARYLOXYPROPANOLAMINE MOIETIES

[75] Inventor: Graham S. Poindexter, Evansville, Ind.

[73] Assignee: Bristol-Myers Company, New York, N.Y.

[21] Appl. No.: 779,188

[22] Filed: Sep. 23, 1985

Related U.S. Application Data

[63] Continuation-in-part of Ser. No. 666,848, Oct. 31, 1984, abandoned.

[51] Int. Cl.$^5$ ............... C07D 211/86; A61K 31/455
[52] U.S. Cl. ......................... 514/356; 514/336; 514/222.8; 514/223.8; 514/231.5; 546/321; 546/284; 544/131
[58] Field of Search ............... 544/131; 546/284, 321; 514/228, 234, 236, 336, 356

[56] References Cited

U.S. PATENT DOCUMENTS 3,485,847 12/1969 Bossert et al. ............... 546/321
4,532,248 7/1985 Franckowink et al. ......... 514/358

FOREIGN PATENT DOCUMENTS 60897 9/1982 European Pat. Off. .
151006 8/1985 European Pat. Off. .
243102 7/1985 Japan .

OTHER PUBLICATIONS

Baldwin et al., *J. Med. Chem.*, 24, pp. 628–631 (1981).
Bossert, F. et al., "4–Aryldihydropyridine", Angew. Chem. Int. Ed. Engl. 20, (1981), pp. 762–769.

*Primary Examiner*—Jane T. Fan
*Attorney, Agent, or Firm*—Robert H. Uloth

[57] ABSTRACT

A series of compounds useful in treating cardiovascular disorders due to the combined expression of both β-block and calcium-block activity by these agents. This useful combination of actions is effected by a novel combination of structural subunits forming these compounds. Essentially, β-blocking aryloxypropanolamine moieties are attached via their aryl ring or amino nitrogen at one of the carboxylate groups of calcium-blocking 4-aryl-1,4-dihydropyridine-3,5-dicarboxylates. These compounds are prepared from new 4-aryl-1,4-dihydropyridine intermediate compounds.

34 Claims, No Drawings

DIHYDROPYRIDIN-3,5-DICARBOXYLATES INCORPORATING ARYLOXYPROPANOLAMINE MOIETIES

CROSS-REFERENCE TO RELATED APPLICATION

This is a continuation-in-part application of Serial No. 666,848 filed October 31, 1984 now abandoned.

BACKGROUND OF THE INVENTION

The present invention concerns the heterocyclic carbon compounds of the 1,4-dihydropyridine class with a 3-carboxylate or carboxamido group linked to an aryloxypropanolamine moiety. These compounds possess bio-affecting properties.

A substantial body of prior art has evolved over the last decade involving compounds of 4-aryl-1,4-dihydropyridine series which have calcium antagonist properties and are useful in the treatment of cardiovascular diseases. These calcium blocking effects appear to mediate vasodilation making these compounds useful in treating angina and hypertension. These structures are typified by nifedipine

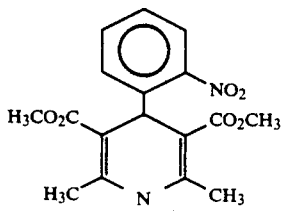
(1)

chemically. 4-nitrophenyl)-2,6-dimethyl-3,5-dicarbomethoxy-1,4-dihydropyridine. Nifedipine and some related 4-aryl-1,4-dihydropyridines are the subject of U.S. Pat. No. 3,485,847 issued Dec. 23, 1969. Numerous subsequent patents have been granted covering 1,4-dihydropyridines in which other substituent groups have been incorporated as the various ring positions of the dihydropyridine moiety via a diversity of chemical bonding groups.

It is currently recognized that dihydropyridine calcium blockers and beta-adrenergic blockers in concert can evoke a greater hemodynamic response than either of the two agents administered individually. Therefore, an object of the instant invention was to design a therapeutic agent combining beta-adrenergic blocking properties with the vasodilation of a calcium blocking agent in a single molecular structure. As far as applicants are aware, the only example of a single molecular structure incorporating both an aryloxypropanolamine and nifedipine-like dihydropyridine structural moiety has been reported by Baldwin, et al., J. Med. Chem., 24, pp. 628-631 (1981). An example of this series of compounds is shown below as Formula 2.

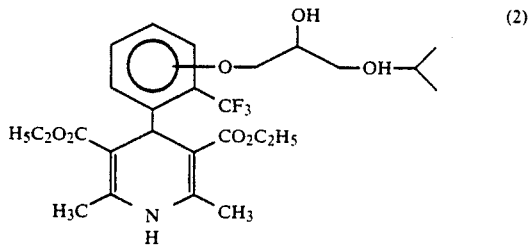
(2)

These compounds, however, did not possess sufficient β-block activity to warrant further interest.

As can be seen, the 4-aryl group of the standard dihydropyridine structure also serves as the aryl group for the aryloxypropanolamine moiety. The compounds of Baldwin, et al. are easily distinguishable structurally over the compounds of the instant invention.

Other related art, although of limited relevancy, can be typified in general by compounds of structure 3 as reported by Araki, et al., European Patent Application 60,897.

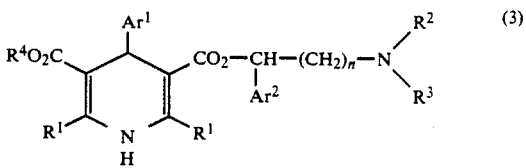
(3)

In structure 3, $R^1$, $R^4$ and $Ar^1$ represent a number of substituent groups which have been previously defined in the voluminous dihydropyridine literature. The groups $R^2$ and $R^3$ may be lower alkyl or aralkyl. These compounds differ significantly from those of the instant invention in that there is no aryloxypropanolamine moiety in the Araki, et al. structure.

In essence, there is nothing in the prior art of which applicants are aware which anticipates or suggests the compounds of the present invention.

SUMMARY AND DETAILED DESCRIPTION OF THE INVENTION

The present invention is concerned with compounds of Formula I and their acid addition salts.

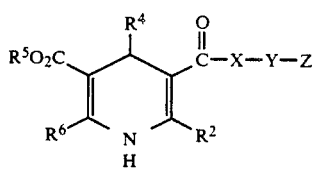
I

In the foregoing structural formula, the symbols $R^2$, $R^4$, $R^5$, $R^6$, X, Y, and Z have the following meanings. $R^2$ is lower alkyl, hydroxyalkyl, alkoxyalkyl, alkylaminoalkyl, dialkylaminoalkyl, phenyl, or thienyl. Lower alkyl means $C_1$-$C_4$; hydroxyalkyl refers to a $C_1$-$C_4$ alkanol chain; alkoxyalky refers to a $C_1$-$C_4$ alkylene chain and a $C_1$-$C_4$ alkyl group connected by an oxygen atom; similarly, alkylaminoalkyl and dialkylaminoalkyl refer to lower alkyl groups and a $C_1$-$C_4$ alkylene chain connected by a secondary (—NH—) or a tertiary

amino group. R⁴ is cycloalkyl of 5-7 carbon atoms, bicycloalkenyl of 7-9 carbon atoms, hetaryl, such as furanyl, indolyl, methylthiopyridyl, thienyl, benzoxadiazolyl, benzothiadiazolyl, and the like; aryl meaning phenyl, naphthyl, or substituted phenyl, with the substituents comprising acetamino, lower alkyl, lower alkoxy, cyano, halogen, hydroxyl, nitro, trifluoromethyl, trifluoromethylsulfonyl, and methylsulfonyl and the like. R⁵ and R⁶ are independently selected from lower alkyl, hyroxyalkyl, alkoxyalkyl, alkylaminoalkyl, or dialkylaminoalkyl and may be the same or different. X is O, NH, or N-alkyl. Y is a covalent bond or a lower alkylene chain which may be substituted with a lower alkyl group, or Y is an alkyleneoxyalkylene, alkyleneaminoalkylene, alkylenecarboxamide, alkylenecarboxamidoalkylene, or alkylenethioureaalkylene chain. Z is a beta-block moiety of Formula A or B

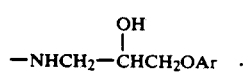

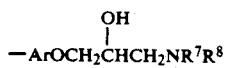

with Ar being naphthyl or phenyl either unsubstituted or optimally substituted at one or more ring positions with lower alkyl, akloxy, alkoxyalkylene, aminocarbonylalkylene, cyano, or halogen and R⁷ and R⁸ are independently chosen from lower alkyl and hydrogen.

Preferred classes of compounds are those in which Z is substructure A and Ar is 2 methylphenyl. Also preferred are the compounds wherein R⁴ is 3-nitrophenyl and X is O. For preferred compounds R², R⁵ and R⁶ are lower alkyl.

The compounds of the present invention can exist as optical isomers and both racemic and diastereomeric mixtures of these isomers as well as the individual optical isomers themselves are within the scope of the present invention. The racemic mixtures can be separated into their individual isomers through well known techniques such as the separation of diastereomeric salts formed with optically active acids, followed by conversion back to the optically active bases. As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, maleic acid, sorbic acid, aconitic acid, salicylic acid, phthalic acid, embonic acid, enanthic acid, and the like.

The compounds of the present invention may be produced, starting with novel dihydropyridine intermediates of Formula II,

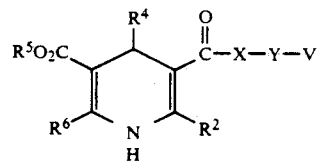

wherein, R², R⁴, R⁵, R⁶, X, and Y are the same as for Formula I and V is amino, halogen, hydroxyphenyl, hydroxynaphthyl, or isothiacyanato, by the following processes which employ epoxide intermediates commonly used in preparative methods for aryloxypropanolamine beta-blockers. The 1,4-dihydropyridine-3,5-dicarboxylate intermediates (II), another aspect of the invention, are obtained from preparative processes which employ variations of the Hantzsch synthetic reaction applied to the appropriate starting materials. Specifically, the modified Hantzsch processes used and many of the required intermediate compounds have been previously described in U.S. Pat. No. 4,414,213 which is hereby incorporated herein by reference.

There are two general processes which are utilized for preparation of the Formula I compounds of this invention. Choice of general process (Schemes 1 or 2) is dependent on selection of the beta-block moiety substructure A or B. The general processes are:

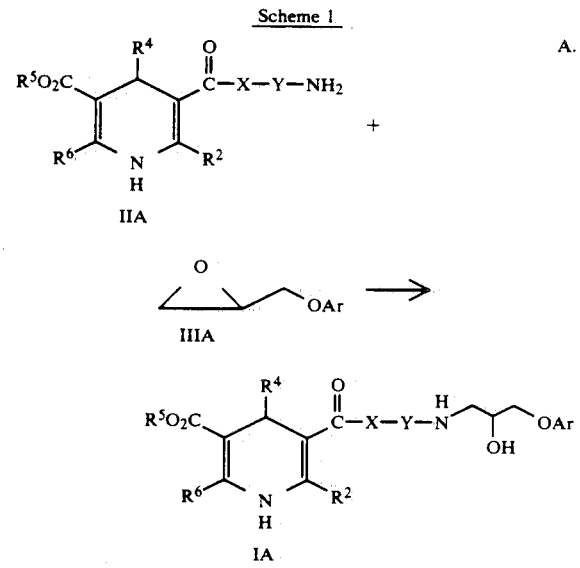

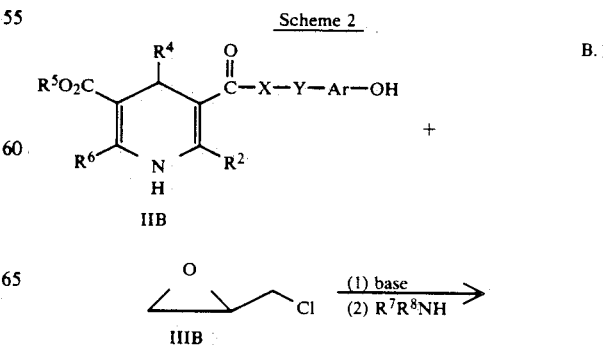

-continued
Scheme 2

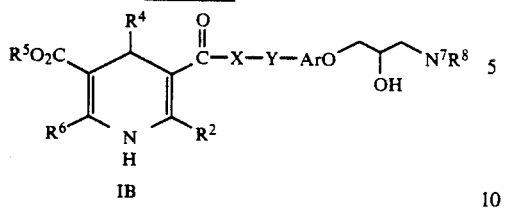

IB

In the foregoing and following general Schemes 1-5, $R^2$, $R^4$, $R^5$, $R^6$, X, Y, and Ar are as defined in Formula I. Preparation of the compounds of Formula I according to the process of Scheme 1 generally comprises heating IIA-type and IIIA-type intermediate compounds neat or in the presence of a wide variety of reaction inert organic solvents. Suitable solvents include but are not limited to benzene, toluene, tetrahydrofurna, dibutyl ether, butanol, hexanol, methanol, dimethoxyethane, ethyleneglycol, ethanol, propanol, etc. Other well known synthetic methods from aryloxypropanolamine beta-blocker chemistry may also be employed and would afford similar IA products. An example of such an alternate synthetic method is illustrated in Scheme 3:

Scheme 3

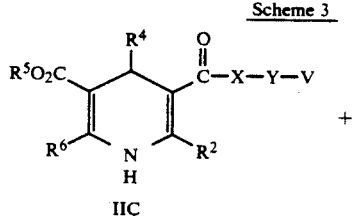

IIC

-continued
Scheme 3

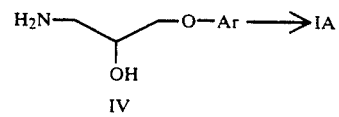

IV wherein V is halogen or —NCS.

In the process of Scheme 2, a phenolic intermediate IIB is treated with a base and epichlorohydrin, giving a glycidol ether reaction intermediate which is converted to a IB product by reaction with an appropriate amine, $HNR^7R^8$. This reaction of a glycidol ether and amine is the same reaction type as in Scheme 1 and similar reaction conditions are employed.

The dihydropyridine intermediates of structure II are generally prepared by way of modified Hantzsch processes as illustrated in Schemes 5 and 6. It is recognized that these intermediates may also be obtained by other methods familiar to a skilled chemical practitioner. As an example (Scheme 4), hydrolytic ring-opening of 3-heterocyclic dihydropyridine salts (XIIC) after prolonged heating, will yield the appropriate IIA intermediate in most instances. This method is, however, limited to those compounds where the XIIC starting material is available.

Scheme 4

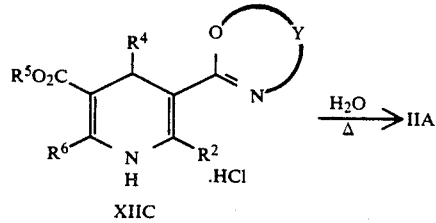

XIIC

In Scheme, 4, XIIC is an acid addition salt, preferably the hydrochloride, and Y is preferably an ethylene or propylene chain, which may be optionally substituted with one or more lower alkyl groups.

Scheme 5
General Preparation of Formula IIA Intermediates

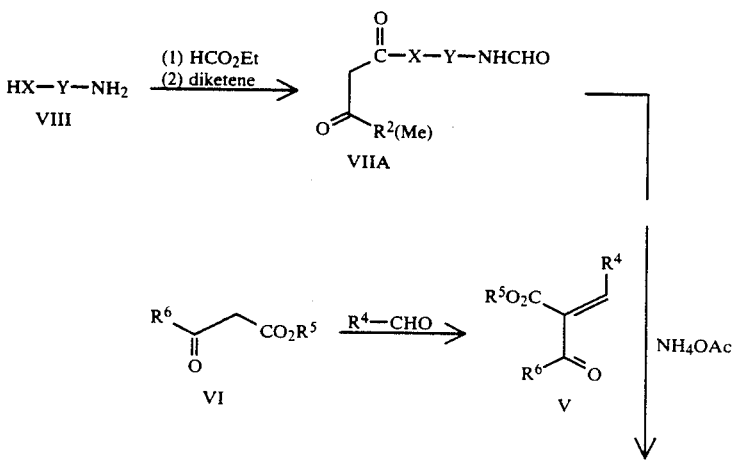

Scheme 5
General Preparation of Formula IIA Intermediates

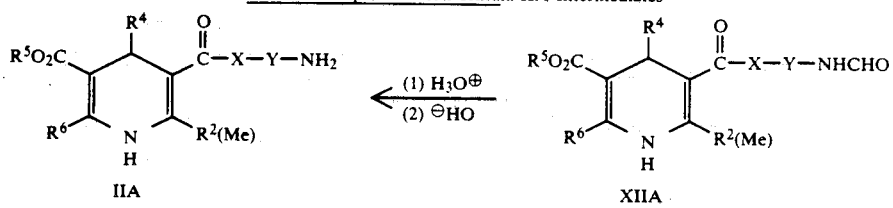

According to Scheme 5, protection of the amino group of intermediate VIII can be accomplished by reaction with ethyl formate. The resulting formamide derivative of VIII is then condensed with diketene yielding the intermediate VIIA. Treatment of VIIA with ammonium acetate followed by Hantzsch condensation with cinnamate V yields the formamido dihydropyridine intermediate compound XIIA. The protecting formyl group is removed by treatment of XIIA with acid followed by neutalization thereby affording the desired formula IIA intermediate.

pared by a modification of Scheme 5 wherein VIII-type starting materials wherein the amino group is replaced by a halogen such as chlorine is used. Additionally IIA compounds may be converted to IC compounds. An example of this would be conversion of a IIA intermediate compound to the corresponding isothiocyanate (IIC) by treatment with thiophosgene in an inert solvent such as methylene chloride.

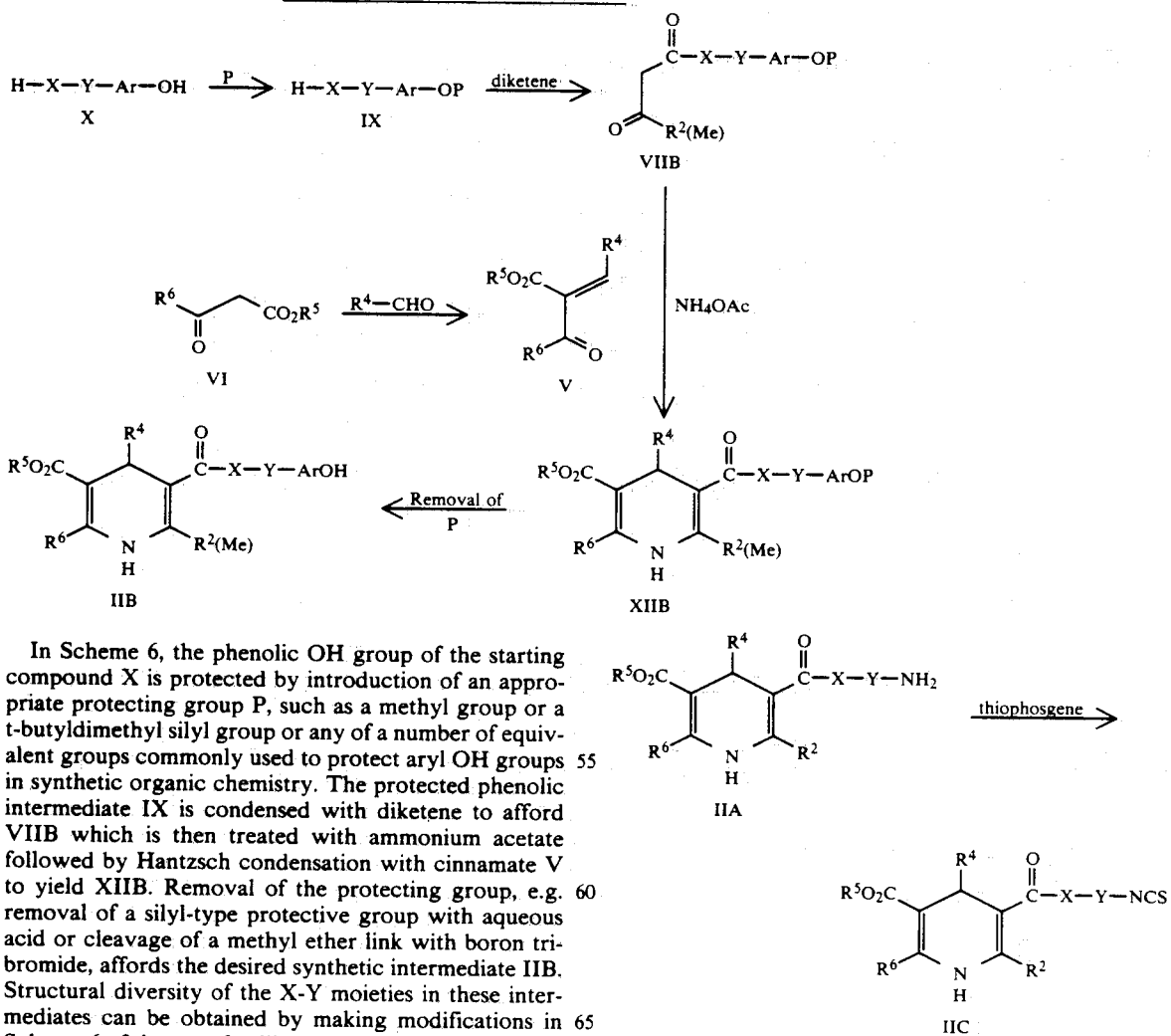

In Scheme 6, the phenolic OH group of the starting compound X is protected by introduction of an appropriate protecting group P, such as a methyl group or a t-butyldimethyl silyl group or any of a number of equivalent groups commonly used to protect aryl OH groups in synthetic organic chemistry. The protected phenolic intermediate IX is condensed with diketene to afford VIIB which is then treated with ammonium acetate followed by Hantzsch condensation with cinnamate V to yield XIIB. Removal of the protecting group, e.g. removal of a silyl-type protective group with aqueous acid or cleavage of a methyl ether link with boron tribromide, affords the desired synthetic intermediate IIB. Structural diversity of the X-Y moieties in these intermediates can be obtained by making modifications in Scheme 6 of the type familiar to a practitioner skilled in the art of organic chemical synthesis. Compounds of Formula IIC (such as used in Scheme 3) can be pre- Some representative compounds will be exemplified in a following section of this specification.

In summary, the synthetic process for preparation of compounds of Formula I comprises:

(1) Reacting (a) a protected amino compound (VIII) or (b) a phenolic compound (X) with ammonium acetate followed by Hantzsch condensation with an appropriate cinnamate (V) to obtain a protected amino or phenolic dihydropyridine intermediate (XII).

(2) Removal of the protective group followed by reaction with (a) an aryloxyepoxide (IIIA), in the case of the amino dihydropyridine intermediate (IIA) to give IA, or (b) with epichlorohydrin (IIIB), in the case of the phenolic dihydropyridine intermediate (IIB) to give a glycidol ether reaction intermediate which is treated with an appropriate primary or secondary amine thereby providing the IB product.

The compounds of this invention have been found to possess cardiovascular pharmacological properties that would be useful in treating cardiovascular disorders such as angina and hypertension. Evaluation of these pharmacological properties was affected by means of both in vitro and in vivo biological screens. In vitro screening included calcium activity in various smooth muscle systems such as rat dorsal aorta, portal vein, and trachea; effects on blood platelets, $\beta$-binding affinities which were determined in rat heart and lung. In general, the preferred compounds of the instant invention possessed calcium entry blockade activity with potencies approaching the reference compound nifedipine; inhibited blood platelet aggregation; and bound to $\beta$-receptors. The $\beta$-binding activity was much greater for the instant compounds than for nifedipine with most members of the present series being one or two orders of magnitude more potent. The in vivo testing included vasodilating results in the ganglion-blocked, angiotensin-II supported rat and antihypertensive screening in the spontaneous hypertensive rat (SHR) or DOCA salt rats. In general, vasodilating activity parelleled calcium blocking activity for members of the instant series. Similarly, the most potent calcium blockers of the instant series also tended to show the greatest effect in reducing blood pressure in hypertensive rat models. $\beta$-Binding affinity was greatest for those preferred compounds in which Z is substructure A and Ar is 2-methyl- or 2-cyano-phenyl. None of the compounds of the instant series demonstrated appreciable $\beta_1$ selectivity.

Considering the biological activities possessed by compounds of the instant series, it can be seen that these compounds have cardiovascular properties particularly suited to their use in angina and especially hypertension. Thus, another aspect of the instant invention concerns a process for ameliorating hypertension in a mammal in need of such treatment which comprises systemic administration to such mammal of an effective dose of a Formula I cmpound or a pharmaceutically acceptable acid addition salt thereof. On the basis of animal testing, an effective dose could be expected to be from about 1 to 50 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for the reference drug nifedipine and the daily oral dose will comprise from about 5 to about 50 mg, preferably 10-20 mg of a Formula I compound administered from 1 to 3 times a day. In some instances, a sufficient therapeutic effect can be obtained at lower doses while in others, larger doses will be required.

The term systemic administration as used herein refers to oral, rectal, and parenteral (i.e. intramuscular, intravenous, and subcutaneous) routes. Generally, it will be found that when a compound of the present invention is administered orally, a larger quantity of the reactive agent is required to produce the same effect as a smaller quantity given parenterally. In accordance with good clinical practice, it is preferred to administer the instant compounds at a concentration level that will produce effective antihypertensive effects without causing any harmful or untoward side effects. Therapeutically, the instant compounds are generally given as pharmaceutical compositions comprised of an effective antihypertensive amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with a pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e. physically discrete units containing a predetermined amount of the drug corresponding to a fraction or multiple of the dose which is calculated to produce the desired therapeutic response. The dosage units can contain one, two, three, or more single doses, or, alternatively, one, one-half, one-third, or less of a single dose. A single dose preferably contains an amount sufficient to produce the desired therapeutic effect upon administration at one application of one or more dosage units according to the pre-determined dosage regimen; usually a whole, half, third, or less of the daily dosage administered once, twice, three, or more times a day. Other therapeutic agents can also be present. Pharmaceutical compositions which provide from about 1 to 50 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol, or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intranveous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethylene glycols or mixtures thereof. The polyethylene glycols consist of a mixture of non-volatile, usually liquid, polyethylene glycols which are soluble in both water and organic liquids and have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), triplet (t), or quartet (q). Abbreviations employed are DMSO-$d_6$ dimethylsulfoxide), CDCl$_3$ (deuterochloroform) and are otherwise conventional. The infrared (IR) spectral descriptions include only absorption wave numbers (cm$^{-1}$) having functional group identification value The IR determinations were employed using potassium bromide (KBr) as diluent. All compounds gave satisfactory elemental analyses.

SYNTHESIS OF INTERMEDIATES

A. Intermediates of Formula IIA

EXAMPLE 1

(3-Aminopropyl) Ethyl 1,4-dihydro-2,6-dimethyl-4-(3-nitrophenyl)-3,5-pyridinedicarboxylate A solution of 3-(formylamino)propyl acetoacetate* (VIIA; 46.8 g; 0.25 mole), ammonium acetate (19.3 g; 0.25 mole), and 250 mL of absolute ethanol was refluxed under nitrogen. After 1.5 hr, ethyl 2-[(3-nitrophenyl)-methylene]-3-oxobutanoate (V: 65.8 g; 0.25 mole) was added to the clear solution and the resulting mixture refluxed an additional 24 hr during which time dissolution occurred. After cooling the yellow solution to room temperature, it was concentrated in vacuo to yield a dark yellow oil. Trituration with 1.5 liter of ethyl ether furnished 67.7 g of the crude formamide intermediate as a yellow solid. After recrystallization from methanol-ethyl ether, 24.3 g (23%) of ethyl [3-(formylamino)propyl]1,4-dihydro-2,6-dimethyl-4-(3-nitrophenyl)-3,5-pyridinedicarboxylate (XIIA) was obtained as a yellow solid, m.p. 137°-138°.

*Intermediates of Formula VIIA were generally prepared by refluxing ethyl formate and the appropriate amine in ethanol for several hours and then concentrating in vacuo to a formamide which is heated to 80° and treated with several drops of triethylamine followed by an equivalent of diketene.

A solution consisting of the formylamino intermediate (XIIA: 24.3 g; 56.4 mmole) in 400 mL of absolute ethanol was treated with concentrated hydrochloric acid (5.0 mL; 60 mmole) and the mixture refluxed under nitrogen for 28 hr. The yellow solution was concentrated in vacuo and the residue dissolved in 400 mL of water and then made basic with conc ammonium hydroxide. The free base was extracted with methylene chloride and the combined organic portions were washed with water and brine. After drying (K$_2$CO$_3$) and filtration, the methylene chloride was removed in vacuo to yield a dark yellow oil. Flash chromatography (chloroform, 5% methanol:chloroform, and then 90:10:1 chloroform:methanol:ammonium hydroxide) afforded 14.3 g of the amine as a yellow oil. Trituration from ethanol yielded 10.9 g (48%) of the desired IIA product as a yellow solid, m.p. 118°-121°.

NMR (CDCl$_3$): 1.22 (3,t, 7.0 Hz); 1.24 (2,bs); 1.73 (2,m); 2.35 (6,s); 2.66 (2,t, 7.0 Hz); 4.08 (2,q, 7.0 Hz); 4.13 (2,m); 5.09 (1,s); 7.35 (1,m); 7.64 (1,m); 8.05 (2,m).

IR (KBr): 700, 1095, 1120, 1210, 1350, 1530, 1650, 1695, 2975, 3330, 3390.

Some examples of IIA compounds prepared by this procedure are shown in Table 1.

TABLE 1

| Ex. | R$^2$ | X | Y | R$^5$ | R$^6$ | m.p. (°C.) XIIA | m.p. (°C.) IIA |
|---|---|---|---|---|---|---|---|
| 2 | CH$_3$ | O | —CH$_2$C(Me)$_2$— | CH$_3$ | CH$_3$ | indistinct | indistinct |
| 3 | CH$_3$ | NH | —CH$_2$CH$_2$— | CH$_3$ | CH$_3$ | indistinct | 143–145 |
| 4 | CH$_3$ | O | —CH$_2$CH$_2$— | CH$_3$ | CH$_3$ | (not isolated) | 150–151 |
| 5 | CH$_3$ | O | —(CH$_2$)$_3$— | CH$_3$ | CH$_3$ | 103–112 | indistinct |

EXAMPLE 6

Ring Opening of 3-Heterocyclic Dihydropyridine Salts: General Procedure (Scheme 4)

To 1.2 L refluxing water was added a solution of 50 mmole of the appropriate heterocyclic dihydropyridine hydrochloride XIIC dissolved in 200 mL of 2-propanol. The resulting yellow solution was allowed to reflux for 5–7 days to complete the hydrolysis as determined by TLC analysis. The completed reaction was allowed to cool to room temperature, and then made basic with conc ammonium hydroxide. After the aqueous mixture was extracted with methylene chloride (3×300 mL), the combined organic extracts were washed with water (100 mL), brine (100 mL), and then dried over anhydrous potassium carbonate. Filtration and concentration in vacuo furnished the crude amines as yellow oils. Purification was either affected by flash chromatography using ammoniated methanol-chloroform solutions (typically 95:5:0.5/CHCl$_3$:CH$_3$O$_2$:conc NH$_4$OH) as eluents, or by trituration with ether to induce crystallization.

EXAMPLE 7

(2-Amino-2,2-dimethylethyl)$^3$ Methyl$^5$2-Ethyl-1,4-dihydro-6-methyl-4-(3-nitrophenyl)-3,5-pyridinedicarboxylate Starting with methyl 3-(4,5-dihydro-4,4-dimethyl-2-oxazolyl)-1,4-dihydro-2-ethyl-6-methyl-4-(3-nitrophenyl)-5-pyridinecarboxylate monohydrochloride and using the procedure of Example 6, a 61% yield of product was obtained as a yellow solid, m.p. 123°–126°.

NMR (CDCl$_3$) 1.03 (3,s); 1.06 (3,s); 1.25 (3,t, 7.1 Hz); 1.30 (2,bs); 2.32 (3,s); 2.81 (2,q, 7.1 Hz); 3.70 (3,s); 3.84 (2,s); 5.17 (1,s); 6.64 (1,bs); 7.38 (1,m); 7.69 (1,m); 8.05 (2,m).

IR (KBr): 710, 1035, 1100, 1125, 1210, 1350, 1500, 1530, 1645, 1690, 1700, 2970, 3340.

Some additional examples of IIA compounds prepared by this procedure are shown in Table 2.

TABLE 2
Formula IIA Intermediates Prepared by Scheme 4

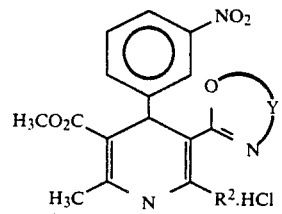

(XIIC)

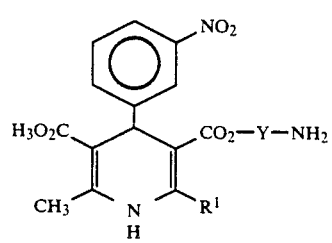

(IIA)

| Ex | R$^2$ | Y | % Yield | m.p. (°C.) |
|---|---|---|---|---|
| 8 | i-C$_3$H$_7$ | —CH$_2$C(Me)$_2$— | 49 | 133–134 |
| 9 | C$_6$H$_5$ | —CH$_2$C(Me)$_2$— | 54 | 135–137 |
| 10 | 2-thienyl | —CH$_2$C(Me)$_2$— | 51 | 152–154 |
| 11 | C$_2$H$_5$ | —CH$_2$CH$_2$— | 29 | indistinct |
| 12 | C$_2$H$_5$ | —CH$_2$CH$_2$CH$_2$— | 43 | indistinct |

Further examples of IIA compounds which may be prepared by adapting the above and other standard methods are shown in Table 3.

TABLE 3
Additional IIA Compounds

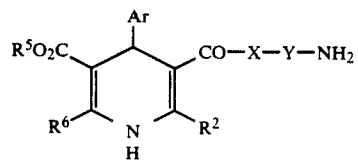

| Ex. | R$^2$ | X | Y | Ar | R$^5$ | R$^6$ |
|---|---|---|---|---|---|---|
| 13 | CH$_3$ | NCH$_3$ | —(CH$_2$)$_2$O(CH$_2$)$_2$— | 2-NO$_2$Ph | CH$_2$CH$_2$OCH$_3$ | CH$_3$ |
| 14 | n-C$_3$H$_7$ | O | —(CH$_2$)$_4$— | 2,3-diClPh | CH$_2$CH$_2$N(CH$_3$)$_2$ | CH$_3$ |
| 15 | CH$_2$CH$_2$N(CH$_3$)$_2$ | O | —(CH$_2$)$_3$— | CH$_3$S-pyridyl | i-C$_3$H$_7$ | n-C$_3$H$_7$ |
| 16 | CH$_3$ | NH | —CH$_2$C(CH$_3$)$_2$— | 3-CNPh | CH$_3$ | CH$_3$ |
| 17 | CH$_2$OCH$_3$ | O | —CH$_2$CH$_2$— | benzofurazanyl | C$_2$H$_5$ | CH$_3$ |
| 18 | CH$_2$CH$_2$OCH$_3$ | NC$_2$H$_5$ | —(CH$_2$)$_2$NH(CH$_2$)$_2$— | benzofurazanyl | CH$_2$CH$_2$OH | CH$_2$CH$_2$NHCH$_3$ |
| 19 | CH$_3$ | O | —(CH$_2$)$_2$NCH$_3$(CH$_2$)$_2$— | 1-naphthyl | CH$_3$ | C$_2$H$_5$ |
| 20 | CH$_3$ | O | —(CH$_2$)$_3$— | 2-CF$_3$Ph | CH$_2$CH(CH$_3$)$_2$ | CH$_3$ |

B. Intermediates of Formula IIB

EXAMPLE 21

Ethyl [2-(4-Hydroxyphenyl)ethyl]1,4-Dihydro-2,6-dimethyl-4-(3-nitrophenyl)-3,5-pyridinedicarboxylate Hydrate A solution of methyl 4-hydroxyphenylacetate (47 g, 0.28 mole), t-butyldimethylchlorosilane (51.1 g, 0.34 mole) and imidazole (48 g, 0.71 mole) in dimethylformamide (100 mL) was heated at 85° for 14 hr. The solution was diluted with water (600 mL) and the mixture extracted with Skelly F. The extracts were washed with dilute base, dried (MgSO$_4$) and concentrated in vacuo to give 89 g of crude product. The crude oil was purified by chromatography (silica eluting with 95:5 Skelly F-ethyl ether) to give 60.7 g (77%) of methyl 4-[(1,1-dimethylethyl)dimethylsiloxl]phenylacetate as a clear oil.

A solution of the above methyl phenylacetate clear oil (41.7 g, 0.15 mole) in 500 mL of tetrahydrofuran was treated with 30 mL of 10 molar BH$_3$·(CH$_3$)$_2$S reagent added at one time. This solution was stirred at reflux for 18 hr. After cooling, 100 mL of water was added and the solution was concentrated to an oil. Trituration of this oil with ethyl ether gave a solid which was removed by filtration and discarded. The filtrate was concentrated and then triturated twice with carbon tetrachloride to remove trace amounts of ethyl ether. A final concentration under reduced pressure yielded 40 g (quantitative) of 2-[4-[(1,1-dimethylethyl)dimethylsiloxyl]phenyl]-ethanol as an oil.

A portion of this oil (25 g, 0.1 mole) was stirred and diketene (8.4 g, 0.1 mole) was added dropwise while keeping the temperature less than 10° C. by use of an ice bath and intermittant addition of triethylamine catalyst. After the addition was completed, the reaction was stirred at 25° for 2 hr. Concentration of the reaction in vacuo removed excess triethylamine. Flash chromatography (SiO$_2$) using chloroform as eluent gave 17.8 g (53%) of 2-[4-[(1,1dimethylethyl)dimethylsiloxyl]phenyl]ethyl acetoacetate as a clear oil.

A solution of this acetoacetate (8.0 g, 0.024 mole), ammonium acetate (1.85 g, 0.025 mole) and ethyl 2-[(3-nitrophenyl)methylene]-3-oxobutanoate (6.3 g, 0.024 mole) in 50 mL of absolute ethanol was refluxed for 3.5 hr with stirring. The reaction was concentrated and the residue dissolved in ethyl ether and washed twice with aqueous sodium carbonate. The dried (potassium carbonate) ethyl ether extract was concentrated to 14.8 g of oil. Trituration with Skelly B gave 12.1 g (87%) of [2-[4-[(1,1-dimethylethyl)dimethylsiloxyl]phenyl]ethyl-]ethyl 1,4-dihydro2,6-dimethyl-4-(3-nitrophenyl)-3,5-pyridinedicarboxylate as a yellow solid, m.p. 120°-130°.

A portion of this yellow silyloxy-ether (5.4 g, 0.009 mole) was refluxed with stirring in 150 mL of 6.5N ethanolic HCl for 0.5 hr. The reaction was concentrated and the residue taken up in 1 N NaOH and washed twice with ethyl ether. The basic aqueous mixture was acidified with 1 N HCl and filtered to give 2.8 g (64%) of the desired IIB product as a yellow solid, m.p. 63°-68°.

NMR (CDCl$_3$): 1.20 (3,t, 7.0 Hz); 2.26 (3,s); 2.30 (3,s); 2.79 (2,t, 6.5 Hz); 4.07 (2,q, 7.0 Hz); 4.21 (2,t,.6.5 Hz); 5.02 (1,s); 6.10 (1,bs); 6.66 (2,m); 6.95 (2,m); 7.10 (1,bs); 7.38 (2,m); 8.00 (2,m).

IR (KBr): 700, 1100, 1120, 1215, 1345, 1510, 1525, 1650, 1675, 2970, 3400.

EXAMPLE 22

Ethyl [3-[[(4-Hydroxyphenyl)amino]carbonyl]propyl]1,4-Dihydro-2,6-dimethyl-4-(3-nitrophenyl)-3,5-pyridinedicarboxylate Hemihydrate 4-Hydroxy-N-(4-methoxyphenyl)butanamide, prepared by the reaction of p-anisidine with butyrolactone, cf: DeFeoand and Strickter, *J. Org. Chem.*, 28, 2915 (1963), (31.4 g, 0.15 mole) and 4 mL of triethylamine in 100 mL of tetrahydrofuran was treated dropwise with diketene (30 g, 0.36 mole). The temperature rose to 50° during the addition. After the addition was complete, the solution was stirred for 2 hr at room temperature and then concentrated in vacuo to yield an oil. Trituration with Skelly B and recrystallization from ethyl acetate afforded 29.8 g (68%) of the corresponding acetoacetate as a tan solid, m.p. 75°-78°.

A portion of this tan solid (5.87 g, 20 mmole) was taken up in 50 mL of ethanol following which ammonium acetate (1.54 g, 20 mmole), and ethyl 2-[(3-nitrophenyl)methylene]-3-oxobutanoate (5.26 g, 20 mmole) were added. After refluxing 25 hr, the solvent was removed and the residue purified by flash chromatography (chloroform) to yield 4.8 g (45%) of ethyl [3-[[(4-methoxyphenyl)amino]carbonyl]propyl]1,4-dihydro-2,6-dimethyl-4-(3-nitrophenyl)-3,5-pyridinedicarboxylate hemihydrate as a yellow foam, m.p. 53°-63°.

A portion of this yellow foam (4.0 g, 7.5 mmole) was taken up in a small amount of methylene chloride under nitrogen and was treated at −10° with 1 N BBr$_3$ (22.5 mL, 0.0225 mole) solution. After 1.5 hr, the hydroscopic solid was filtered and then added immediately to saturated sodium bicarbonate, producing a gummy solid. This gum was dissolved in 1 N NaOH and yielded on acidification 1.5 g of solid. Flash chromatography using chloroform (2% methanol) followed by chloroform (4% methanol) gave 0.75 g of product. This residue was dissolved in aqueous sodium hydroxide and gave 0.6 g (15%) of the desired IIB product on acidification, m.p. 95°-105°.

EXAMPLE 23

[2-[[[(4-Hydroxyphenyl)methyl]carbonyl]amino]-2,2-dimethylethyl][3] Methyl[5] 2-Ethyl-1,4-dihydro-6-methyl-4-(3-nitrophenyl)-3,5-pyridinedicarboxylate Hydrate A solution of 4-hydroxyphenylacetic acid (4.56 g, 0.03 mole) in 125 mL of tetrahydrofuran at 50° was treated in portions with 1,1-carbonyldiimidazole (6.4 g, 0.04 mole) and stirred until the CO$_2$ evolution stopped. A solution of (2-amino-2,2-dimethylethyl)[3] methyl[5] 2-ethyl-1,4-dihydro-6-methyl-4-(3-nitrophenyl)-3,5-pyridinedicarboxylate (prepared by the procedure of Example 3, 12.5 g, 0.04 mole) in 50 mL of tetrahydrofuran was added. The resulting solution was stirred at 25° for 16 hr. The solution was concentrated and the residue was dissolved in chloroform and washed with water and dilute HCl. The dried (Na$_2$SO$_4$) chloroform layer was concentrated to 15.4 g of oil. Flash chromatography using chloroform then chloroform (2% methanol) yielded 4.4 g (27%) of IIB product as a yellow foam, m.p. 70°-80°.

EXAMPLE 24

Ethyl 1,4-Dihydro-5-[[(4-hydroxyphenyl)amino]carbonyl]-2,6-dimethyl-4-(3-nitrophenyl)-3-pyridinecarboxylate Diketene (0.20 mole) was slowly added to a mixture of p-aminophenol (10.9 g, 0.100 mole) and 50 mL of tetrahydrofuran with stirring, during which time exothermic heating and dissolution occurred. The solvent was removed in vacuo and the solid residue taken up in 200 mL of absolute ethanol. Ammonium acetate (7.8 g, 0.11 mole) was added and the solution was refluxed under nitrogen for 1.5 hr. Ethyl 2-[(3-nitrophenyl)methylene]-3-oxobutanoate (26.3 g, 0.100 mole) was then added and the solution refluxed 4 hr under nitrogen. The solution was concentrated in vacuo and the yellow residue taken up in methylene chloride and extracted with 10% aqueous sodium hydroxide. The combined basic extracts were made acid with conc HCl and then extracted with methylene chloride. The combined organic phases were washed with water and dried over $MgSO_4$. Filtration and concentration in vacuo afforded 33 g of orange solid. Recrystallization from ethanol-:ethyl ether furnished 8.0 g (18%) of the desired IIB product as a pale yellow solid, m.p. 223°–224°.

A variety of intermediates of Formula IIB can be prepared by employing the appropriate synthetic procedure from among those given in Examples 21 α 24.

C. Intermediates of Formula IIC

EXAMPLE 25

(2-Isothiacyanatoethyl) Methyl 1,4-dihydro-2,6-dimethyl-4-(3-nitrophenyl)-3,5-pyridinedicarboxylate A solution of thiophosgene (0.77 mL, 10.0 mmole) in 30 mL of chloroform was added to a stirred solution of (2-aminoethyl) methyl 1,4-dihydro-2,6-dimethyl-4-(3-nitrophenyl)-3,5-pyridinedicarboxylate (prepared using the procedure of Example 1; 3.75 g, 10.1 mmoles) and triethylamine (2.10 g, 20.0 mmole), in 50 mL of chloroform and stirred 30 minutes at ambiant temperature. The resulting dark solution was washed with water (2×20 mL) and dried over anhydrous sodium sulfate. After filtration, the solvent was removed in vacuo to yield 3.5 g of dark oil. Trituration with ether furnished 2.85 g (69% yield) of the isothiacyanato intermediate as a yellow solid, m.p. 163°–164°.

EXAMPLE 26

(3-Chloropropyl) Methyl 1,4-Dihydro-2,6-dimethyl-4-(3-nitrophenyl)-3,5-pyridinedicarboxylate 3-Chloropropanol (47.3 g, 0.500 mole) and a catalytic amount of triethylamine at 65° were treated dropwise with diketene (42 g, 0.50 mole). After the addition was complete, the reaction was stirred at 65° for an additional hour. Distillation of the residue furnished 72.9 g (82%) of 3-chloropropyl acetoacetate as a clear liquid, b.p. 78°–85° at 150 torr.

Ammonium acetate (3.85 g, 50.0 mmole) was added to a solution of 3-chloropropyl acetoacetate (8.25 g, 50.0 mmole) and 50 mL of absolute ethanol, and then refluxed under nitrogen for one hour. Methyl 2-[(3-nitrophenyl)methylene]-3-oxobutanoate, prepared by the condensation of 3-nitrobenzaldehyde with methyl acetoacetate; (12.5 g, 50.0 mmole) was then added and the resulting yellow solution refluxed an additional 12 hr. After cooling to room temperature, the solvent was removed in vacuo and the residue recrystallized from ethanol to yield the desired IIC product as a yellow solid, m.p. 125°–130°.

NMR (DMSO-$d_6$): 2.04 (2,m); 2.35 (6,s); 3.42 (2,t, 6.5 Hz); 3.64 (3,s); 4.20 (2,t, 6.3 Hz); 5.07 (1,s); 7.40 (2,m); 7.64 (1,m); 8.05 (2,m).

IR (KBr): 705, 1100, 1120, 1215, 1350, 1490, 1530, 1650, 1685, 1700, 3370.

D. Intermediates of Formula III

Aryl glycidol ethers (IIIA) are readily prepared by standard epichlorohydrin/piperidine reactions utilizing the appropriate starting phenol. The following example illustrates preparation of a IIIA intermediate compound.

EXAMPLE 27

1-(2-Methoxyethyl)-4-(oxiranylmethoxy)benzene

A solution of $BH_3.(CH_3)_2S$ (500 mL, 2M in tetrahydrofuran) was added dropwise to a solution of methyl 4-hydroxyphenylacetate (116 g, 0.70 mole) in 300 mL dry tetrahydrofuran. This solution was heated at reflux for 2 hr and stirred at room temperature for 12 hr. TLC indicated the presence of phenol and another 30 mL of $BH_3.(CH_3)_2S$ solution was added. This solution was refluxed for 1 hr, cooled, and then hydrolyzed by dropwise addition of water. The mixture was concentrated in vacuo and the residue triturated with ethyl ether. The ethyl ether portion was dried ($MgSO_4$) and concentrated in vacuo to give 90 g (93%) of 4-(2-hydroxyethyl)phenol, m.p. 84°–86°.

A solution of this hydroxyethylphenol (5.0 g, 0.036 mole) in 20 mL of 48% HBr was heated at reflux for 1.5 hr during which time an oil separated. The mixture was cooled and extracted with methylene chloride. The extracts were dried ($MgSO_4$) and concentrated in vacuo. The residue was recrystallized from hexane to give 4.0 g (55%) of 4-(2-bromoethyl)phenyl as a white solid product, m.p. 87°–89°.

The 4-(2-bromoethyl)phenol was converted into 4-(2 methoxyethyl)phenol in nearly quantitative yield using the method of Baird and Weinstein, JACS, 85:565 (1963) ($AgNO_3$ and methanol). The clear oil was used without further purification.

A solution of the methoxyethyl phenol (68 g, 0.45 mole) and epichlorohydrin (280 g, 3.0 mole) were heated with a few drops of piperidine at 120° for 3 hr. The excess epichlorohydrin was removed in vacuo and the residue dissolved in tetrahydrofuran (100 mL). A solution of NaOH (24 g, 0.6 mole) in 200 mL water was added and the mixture was stirred at room temperature for 2 hr. The tetrahydrofuran was removed in vacuo and the residue triturated with ethyl ether. The ethyl ether was removed in vacuo to give 55 g (59%) of crude epoxide . product. A portion of the oil was distilled to give the pure epoxide, b.p. 120°–125/0.05 Torr.

Synthesis of Products

A. Products of Formula IA

EXAMPLE 28

General Method For The Preparation of Aryloxypropanolaminoalkyl Dihydropyridine, IA A solution of 5 mmoles of the appropriate amine of Formula IIA, 5 mmoles of the appropriate epoxide IIIA in 25 mL of 2-propanol is refluxed under nitrogen for 18-24 hr as determined by TLC analysis. The yellow solutions are concentrated in vacuo and the coupled products purified by flash chromatography using methanol/chloroform solutions as eluents. Some examples of IA products prepared by this procedure are shown in Table 4.

TABLE 4

Products of Formula IA

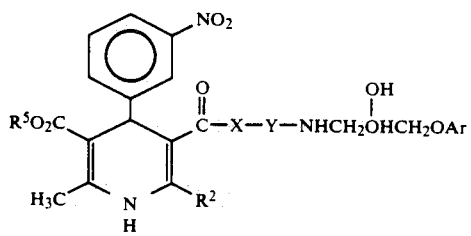

| Ex. | $R^2$ | $R^5$ | X | Y | Ar | % Yield | m.p. (°C.) |
|---|---|---|---|---|---|---|---|
| 29 | $CH_3$ | $CH_3$ | O | $-CH_2C(Me)_2-$ | 2-CNPh | 51 | indistinct |
| 30 | $C_2H_5$ | $CH_3$ | O | $-CH_2C(Me)_2-$ | 2-CNPh | 53 | indistinct |
| 31 | i-$C_3H_7$ | $CH_3$ | O | $-CH_2C(Me)_2-$ | 2-CNPh | 50 | indistinct |
| 32 | Ph | $CH_3$ | ) | $-CH_2C(Me)_2-$ | 2-CNPh | 37 | 189-191 |
| 33 | 2-thienyl | $CH_3$ | O | $-CH_2C(Me)_2-$ | 2-CNPh | 33 | 184-186 |
| 34 | $C_2H_5$ | $CH_3$ | O | $-CH_2CH_2-$ | 2-CNPh | 40 | indistinct |
| 35 | $C_2H_5$ | $CH_3$ | O | $-CH_2CH_2CH_2-$ | 2-CNPh | 58 | indistinct |
| 36 | $CH_3$ | $CH_3$ | NH | $-CH_2CH_2-$ | 2-CNPh | 29 | indistinct |
| 37 | $C_2H_5$ | $CH_3$ | O | $-CH_2C(Me)_2-$ | 2-$CH_3$Ph | 33 | 94-98 |
| 38 | $C_2H_5$ | $CH_3$ | O | $-CH_2C(Me)_2-$ | 2-BrPh | 47 | 108-120 |
| 39 | $C_2H_5$ | $CH_3$ | O | $-CH_2C(Me)_2-$ | 4-MeO$CH_2CH_2$Ph | 33 | indistinct |
| 40 | $CH_3$ | $C_2H_5$ | O | $-CH_2CH_2CH_2-$ | 2-$CH_3$Ph | 28 | 75-80 |
| 41 | $CH_3$ | $CH_3$ | O | $-CH_2CH_2CH_2-$ | 3-$CH_3$Ph | 24 | 85-100 |
| 42 | $CH_3$ | $CH_3$ | O | $-CH_2CH_2CH_2-$ | 4-F-2-$CH_3$Ph | 40 | indistinct |
| 43 | $CH_3$ | $C_2H_5$ | O | $-CH_2CH_2CH_2-$ | 2-CNPh | 21 | indistinct |

EXAMPLE 44

Methyl [3-[[3-(2-Methylphenoxy)-2-hydroxypropyl]-amino]-propyl]1,4-Dihydro-2,6-dimethyl-4-(3-nitrophenyl)-3,5-pyridinedicarboxylate Hydrochloride This example is an illustration of Scheme 3. A mixture of (3-chloropropyl) methyl 1,4-dihydro-2,6-dimethyl-4-(3-nitrophenyl)-3,5-pyridinedicarboxylate (Ex. 24; 6.67 g, 16.3 mmole), 1-amino-3-(2-methylphenoxy)-2-propanol (2.95 g, 16.3 mmole) micropulverized $K_2CO_3$ (2.2 g, 16 mmole), NaI (50 mg), and 75 mL of dry acetonitrile were refluxed 64 hr under nitrogen. The crude reaction mixture was concentrated, dissolved in methylene chloride, and washed with water and brine and dried over $MgSO_4$. Removal of the volatile substances in vacuo furnished a crude oil which was purified by flash chromatography (chloroform, methanol:chloroform, and then 95:5:0.5 chloroform:methanol, $NH_4OH$) to yield 2.85 g of the base as a yellow oil. Conversion to the hydrochloride salt by treatment with 10% aqueous HCl and extraction with methylene chloride afforded 2.4 g (27%) of this IA product as a yellow solid, m.p. 100°-112° C.

NMR (DMSO-$d_6$): 2.18 (2,m); 2.21(3,s); 2.39 (6,s); 3.04 (4,m); 3.59 (3,s); 4.11 (5,m); 5.05 (1,s); 5.50 (1,bs); 7.00 (4,m); 7.65 (2,m); 8.01 (2,m); 9.25 (2,bs); 9.38 (1,bs).

IR (KBr): 705, 1100, 1120, 1215, 1350, 1495, 1530, 1650, 1685, 1700, 2800, 2960.

EXAMPLE 45

[2-[3-[4-(Aminocarbonyl)methyl]phenoxy]-2-hydroxy propyl]amino]-2,2-dimethylethyl]³ Methyl⁵ 2-Ethyl-1,4-dihydro-6-methyl-4-(3-nitrophenyl)-3,5-pyridinedicarboxylate Hemihydrate A solution of IIA intermediate (2-amino-2,2-dimethylethyl)³ methyl⁵ 2-ethyl-1,4-dihydro-6-methyl-4-(3-nitrophenyl)-3,5-pyridinedicarboxylate (8.3 g, 20 mmole) and 4-(oxyiranylmethoxy)benzeneacetamide (4.1 g, 20 mmole) in 300 mL of ethanol was heated at reflux for 30 hr. The solution was concentrated in vacuo and the resulting residue was purified by flash chromatography (2% methanol:chloroform with 0.1% ammonia) on alumina to give 4.2 g (51%) of product as a yellow foam, m.p. 78°-90°.

EXAMPLE 46

Methyl [2-[[[[2-[[2-Hydroxy-3-(2 methylphenoxy)-propyl]amino]ethyl]amino]thiocarbonyl]aminoethyl]1,4-Dihydro-2,6-dimethyl-4-(3-nitrophenyl)-3,5-pyridinedicarboxylate To a solution of the IIC intermediate (2-isothiacyanatoethyl) methyl 1,4-dihydro-2,6-dimethyl-4-(3-nitrophenyl)-3,5-pyridinedicarboxylate (Ex. 25; 1.28 g, 3.07 mmoles) in 15 mL of methylene chloride, was added a solution of 1-[N-(2-aminoethyl)amino]-3-(2-methylphenoxy)-2-propanol; prepared from reaction of 2 methylphenyl glycidol ether and ethylenediamine; 0.72 g, 3.2 mmoles) in 4 mL of methylenechloride. After five minutes the reaction was complete and the solution was concentrated in vacuo. Flash chromatography (chloroform, 2.5% methanol:chloroform, and then 95:5:0.5/ chloroform:methanol:conc $NH_4OH$/silica gel) furnished 0.42 g of product as a yellow solid, m.p. 125°-130°.

Further examples of IA compounds which may be prepared by adapting the examples and other standar methods are shown in Table 5.

TABLE 5

Additional IA Compounds

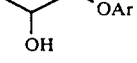

| Ex. | R² | X | Y | Ar | Ar' | R⁵ | R⁶ |
|---|---|---|---|---|---|---|---|
| 47 | CH₃ | NCH₃ | —(CH₂)₂O(CH₂)₂— | 4-H₂NCOCH₂Ph | 2-NO₂Ph | CH₂CH₂OCH₃ | CH₂OH |
| 48 | n-C₃H₇ | O | —(CH₂)₄— | 2-allyloxyphenyl | 2,3-diClPh | CH₂CH₂N(CH₃)₂ | CH₃ |
| 49 | CH₂CH₂N(CH₃)₂ | NH | —(CH₂)₃— | 2-cyclohexylphenyl |  | i-C₃H₇ | CH₃ |
| 50 | CH₂OCH₃ | NC₂H₅ | —CH₂C(CH₃)₂— | 2-i-C₃H₇Ph | 3-CF₃Ph | CH₃ | CH₃ |
| 51 | CH₃ | O | —CH₂CH₂— | 1-naphthyl | 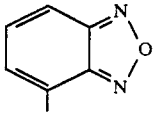 | C₂H₅ | CH₃ |
| 52 | CH₂CH₂NHCH₃ | O | —(CH₂)₂N(CH₂)₂— | 2-ClPh | 1-naphthyl | CH₂CH(CH₃)₂ | CH₃ |
| 53 | n-C₄H₉ | O | —(CH₂)₃N(CH₂)₂—<br>\|<br>CH₃ | 2-FPh | 2-CF₃Ph | C₂H₅ | C₂H₅ |

B. Products of Formula IB

EXAMPLE 54

Ethyl
[2-[4-[3-[2-Hydroxy.(1-methylethyl)-amino]propoxy]-phenyl]ethyl]1,4-Dihydro-2,6-dimethyl-4-(3-nitrophenyl)-3,5-pyridine dicarboxylate Hydrochloride Hydrate Ethyl [2-(4-hydroxyphenyl)ethyl]1,4-dihydro-2,6-dimethyl-4-(3-nitrophenyl)-3,5-pyridinedicarboxylate hydrate (Ex. 21; 1.4 g, 1.8 mmole) and 3 mL of 1 N NaOH in 25 mL of 50% aqueous propanol was treated with epichlorohydrin (0.6 g, 0.006 mole). The resulting solution was stirred at 25° under nitrogen for 72 hr. The solvent was concentrated under reduced pressure and the residue purified on a florisil column with chloroform elution yielding 1.14 g (73%) of ethyl [2-[(4-oxiranylmethoxy)phenyl]ethyl]1,4-dihydro-2,6-dimethyl-4-(3-nitrophenyl)-3,5-pyridinedicarboxylate as an oil which was then refluxed for 3 hours with an excess of isopropyl amine in 25 mL of absolute ethanol. The solvent was removed in vacuo and the residue treated with ethanolic HCl to yield 1.1 g (79%) of the hydrochloride salt as a yellow foam, m.p. 70°-75°.

NMR (DMSO-d₆) 1.20 (3,t, 7.0 Hz); 1.34 (3,s); 1.41 (3,s); 2.29 (3,s); 2.32 (3,s); 2.80 (2,m); 3.20 (3,m); 4.08 (7,m); 4.98 (1,s); 5.00 (1,bs); 6.78 (2,m); 7.05 (2,m); 7.47 (2,m); 7.98 (2,m); 8.88 (1,bs); 9.02 (2,bs).

IR (KBr): 700, 1100, 1115, 1215, 1350, 1510, 1525, 1650, 1680, 2980.

EXAMPLE 55

Ethyl
[2-[4-[3-[(1,1-dimethylethyl)amino]-2-hydroxypropoxy]phenyl]ethyl]1,4-Dihydro-2,6-dimethyl-4-(3-nitrophenyl)-3,5-pyridinedicarboxylate Hydrochloride Hemihydrate This IB analog was prepared using the methodology of Example 44 with t-butylamine being employed in place of isopropylamine. The reaction furnished 1.1 g (79%) of product as a yellow foam, m.p. 75°-85°.

EXAMPLE 56

Ethyl
[3-[[[4-[2-Hydroxy-3-[(1-methylethyl)amino]-propoxy]-phenyl]amino]carbonyl]propyl]1,4-Dihydro-2,6-dimethyl-4-(3-nitrophenyl)-3,5-pyridinedicarboxylate Hydrate A solution of ethyl [3-[[(4-hydroxyphenyl)amino]carbonyl]propyl]1,4-dihydro-2,6-dimethyl-4-(3-nitrophenyl)-3,5-pyridinedicarboxylate hemihydrate (Ex. 22; 2.66 g, 5 mmole) in 50 mL of 50% aqueous 2-propanol with 5 mL of 1 N NaOH and epichlorohydrin (0.92 g, 10 mmole) was refluxed under nitrogen for 4.5 hr. The solvent was removed in vacuo and the resulting residue taken up in methylene chloride and washed with aqueous sodium hydroxide. After drying, the methylene chloride was removed in vacuo to yield 2.1 g of clear oil. Chromatography on florisil (methanol: chloroform) gave 1.6 g (55%) of the epoxide intermediate which was dissolved in 30 mL of ethanol and treated with 5 mL of isopropylamine. After refluxing for 16 hr, the solvent was removed in vacuo and the mixture purified by chromatography on florisil methanol., chloroform with ammonia added) to furnish 1.0 g (55%) of yellow solid product, m.p. 60°-70°.

EXAMPLE 57

[2-[4-[2-Hydroxy-3-[(1-methylethyl)amino]propoxy]-phenyl]methyl]carbonyl]amino]-2,2-dimethylethyl]³ Methyl⁵
2-Ethyl-1,4-dihydro-6-methyl-4-(3-nitrophenyl)-3,5-pyridinedicarboxylate Hemihydrate

[2-[[[(4-Hydroxyphenyl)methyl]carbonyl]amino]-2,2-dimethylethyl]³ methyl⁵ 2-ethyl-1,4-dihydro-6-methyl-4-(3-nitrophenyl)-3,5-pyridinedicarboxylate (Ex. 23;

3.36 g, 6 mmole) in 75 mL of 50% aqueous isopropanol with 6 mL of 1 N NaOH was treated with a large excess of epichlorohydrin (2.8 g, 0.03 mole). The solution was stirred at 25° for 16 hr. The solvent was concentrated to give 4.0 g of the epoxide oil which was taken up in 75 mL of absolute ethanol and refluxed with a large excess (15 mL) of isopropylamine for 2 hr. The reaction solution was concentrated in vacuo to 4.0 g of oil. Flash chromatography using methanol:chloroform mixtures gave 2.6 g (64%) of product as a yellow foam, m.p. 70°–80°.

EXAMPLE 58

Ethyl 1,4-Dihydro-5-[[[4-[2-hydroxy-3-[(1-methylethyl)amino]propoxy]phenyl]amino]carbonyl-2,6-dimethyl-4-(3-nitrophenyl)-3-pyridinecarboxylate Using the procedure of Example 40 and starting with the hydroxyphenyl amide prepared in Example 24, the desired product was obtained in 8% yield as a yellow solid, m.p. indistinct.

FURTHER DETAILED DESCRIPTION OF THE INVENTION

Some additional compounds which are similar to those defined hereinabove by Formula I have been made and tested and found to have useful cardiovascular properties. These compounds, as well as the other compounds of Formula I, supra., are useful for treating cardiovascular disorders such as angina and hypertension. These additional compounds which are new products of Formula IA, supra., are prepared by the general method given as Example 28, supra. These additional compounds are embodied as Formula I'A

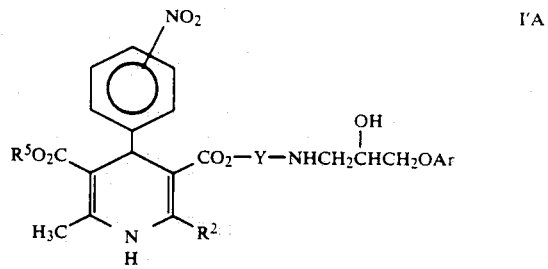

For compounds of Formula I'A: $R^2$, $R^5$, and Y are as previously defined for compounds of Formula I. The definition for Ar, however, is expanded in Formula I'A to include trifluoromethylphenyl, cyclohexylphenyl, allylphenyl, 5,6,7,8-tetrahydro-5-oxo-1-naphthalenyl; 5,6,7,8-tetrahydro-6,7-cis-dihydroxy-1-naphthalenyl; and 4-(4-morpholinyl)-1,2,5-thiadiazol-3-yl moieties. Support for extending the definition of Ar is provided by representative compounds exemplified below in Table 6 as I'A compounds.

TABLE 6

Formula I'A Compounds

| Ex. | $R^2$ | $R^5$ | Y | Ar | m.p. (°C.) | Mol. Formula[a] |
|---|---|---|---|---|---|---|
| 59 | $CH_3$ | $CH_3$ | $-C_3H_6-$ | 1-naphthyl | 75–82 | $C_{32}H_{35}N_3O_8 \cdot 0.2\,H_2O$ |
| 60 | $CH_3$ | $CH_3$ | $-C_3H_6-$ | 2-$CF_3$—Ph | 55–65 | $C_{29}H_{32}F_3N_3O_8$ |
| 61 | $CH_3$ | $CH_3$ | $-C_3H_6-$ | 2-cyclohexyl-Ph | indistinct | $C_{34}H_{43}N_3O_8 \cdot HCl$ |
| 62 | $CH_3$ | $CH_3$ | $-C_3H_6-$ | 2-allyl-Ph | indistinct | $C_{31}H_{37}N_3O_8 \cdot HCl$ |
| 63 | $CH_3$ | $CH_3$ | $-C_3H_6-$ | 5,6,7,8-tetrahydro-5-oxo-1-naphthalenyl | 110–125 | $C_{32}H_{37}N_3O_9 \cdot HCl$ |
| 64 | $CH_3$ | $CH_3$ | $-C_3H_6-$ | 5,6,7,8-tetrahydro-6,7-dihydroxy-1-naphthalenyl | indistinct | $C_{32}H_{39}N_3O_{10} \cdot HCl \cdot H_2O$ |
| 65 | $CH_3$ | $CH_3$ | $-C_3H_6-$ | 4-(4-morpholinyl)-1,2,5-thiadiazol-3-yl | 110–120 | $C_{28}H_{36}N_6O_9S \cdot HCl \cdot 0.9\,H_2O$ |

[a]The C, H, and N elemental analyses were within ± 0.4% of theory for each molecular formula displayed.

The scope of the instant invention is hereby expanded to include the compounds defined by Formula IA as well as those heretofore embraced by Formula I. The present subject matter can now be defined by Formula XXI (shown below) which is comprised of the compounds of Formula I and I'A

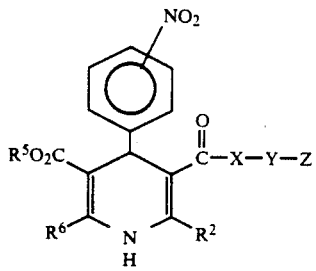

and the pharmaceutically acceptable acid addition salts thereof wherein $R^2$ is lower $C_{1-4}$ alkyl, hydroxylalkyl, alkoxyalkyl, alkylaminoalkyl, dialkylaminoalkyl, phenyl or thienyl; and $R^5$ and $R^6$ are independently selected from lower alkyl, hydroxyalkyl, alkoxyalkyl, alkylaminoalkyl, or dialkylaminoalkyl and may be the same or different. X can be oxygen, thereby producing an ester function, or X may be NH or N-alkyl, thereby producing an amido function. Y is a covalent bond or a lower alkylene chain which may be substituted with a lower alkyl group, or is an alkyleneoxyalkylene, alkyleneaminoalkyl, alkylenecarboxamide, alkylenecarboxamidoalkylene, or alkylenethioureaalkylene chain; and Z is a beta-block moiety of Formula A or B

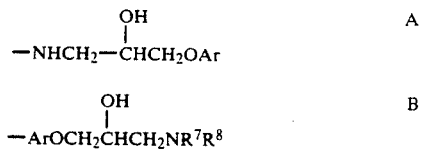

with Ar being naphthyl; 5,6,7,8-tetrahydronaphthyl, which can be substituted at one or more positions in the saturated ring with oxo or hydroxy groups; phenyl, either unsubstituted or optimally substituted at one or more ring positions with lower alkyl, alkoxy, alkoxyalkylene, $(C_{3-6})$cycloalkyl, allyl, aminocarbonylalkylene, cyano, halogen, hydroxyl, or trifluoromethyl; or 4-(4-morpholino)-1,2,5-thiadiazol-3-yl. $R^7$ and $R^8$ are independently chosen from lower alkyl and hydrogen.

The biological testing utilized has been discussed, supra., and biological test data obtained for representative XXI compounds selected for testing is shown in Table 7.

TABLE 7

Biological Test Data For Selected Formula XXI Compounds Wherein X = O

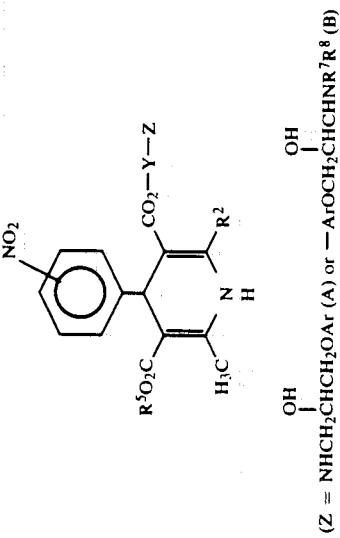

(Z = NHCH$_2$CHCH$_2$OAr (A) or -ArOCH$_2$CHCHNR$^7$R$^8$ (B))

| Ex. No. | R$^2$ | R$^5$ | Y | Z (Ar) | Calcium (pA$_2$)[a] | β-Binding (IC$_{50}$)[b] | Vasodilation[c] (at 0.1 mg/kg) |
|---|---|---|---|---|---|---|---|
| — | Nifedipine (reference agent) | | | | 9.5 | >10$^{-6}$ | 23% (at 0.1 mg/kg) |
| — | Sotalol (reference agent) | | | | | 8 × 10$^{-7}$ | 17% |
| 34 | Et | Me | —C$_2$H$_4$— | A (2-CNPh) | 7.9 | 6 × 10$^{-6}$ | 50 |
| 30 | Et | Me | —CH$_2$CMe$_2$— | A (2-CNPh) | 8.4 | 2 × 10$^{-7}$ | 9 |
| 31 | i-Pr | Me | —CH$_2$CMe$_2$— | A (2-CNPh) | —[d] | 8 × 10$^{-7}$ | 58 |
| 37 | Et | Me | —CH$_2$CMe$_2$— | A (2-MePh) | — | — | 55 |
| 38 | Et | Me | —CH$_2$CMe$_2$— | A (2-BrPh) | — | 1.8 × 10$^{-7}$ | 22[e] |
| 32 | Ph | Me | —CH$_2$CMe$_2$— | A (2-CNPh) | — | 3 × 10$^{-7}$ | 28 |
| 35 | Et | Me | —C$_3$H$_6$— | A (2-CNPh) | — | 2 × 10$^{-7}$ | 12 |
| 33 | 2-thienyl | Me | —CH$_2$CMe$_2$— | A (2-CNPh) | 8.8 | 7 × 10$^{-8}$ | 54 |
| 39 | Et | Me | —CH$_2$CMe$_2$— | A (4-MeOCH$_2$CH$_2$Ph) | 8.2 | 4 × 10$^{-7}$ | 52 |
| 29 | Me | Me | —CH$_2$CMe$_2$— | A-(2-CNPh) | 6.6 | 2 × 10$^{-8}$ | 22 |
| 46 | Me | Me | —[CH$_2$CH$_2$NH]$_2$C—S | A (2-MePh) | 7.9 | — | 57 |
| 54 | Et | Me | —C$_2$H$_4$— | B | 7.9 | 1 × 10$^{-7}$ | [f] |
| 55 | Et | Me | —C$_2$H$_4$— | B | 8.0 | # × 10$^{-8}$ | — |
| 56 | Me | Et | —C$_3$H$_6$CONH— | B | 8.2 | 6.2 × 10$^{-7}$ | — |
| 43 | Me | Et | —C$_3$H$_6$— | A (2-CNPh) | | | |
| 45 | Me | Et | —CH$_2$CMe$_2$— | $\overset{O}{\underset{\|}{\|}}$ A (4-H$_2$NCCH$_2$Ph) | 8.2 | 4.2 × 10$^{-7}$ | 33 |
| 57 | Me | Et | —CH$_2$CMe$_2$— | B | 7.3 | >10$^{-6}$ | 11 |
| 44 | Me | Me | —C$_3$H$_6$— | A (2-MePh) | 7.8–8.0 | 1 × 10$^{-8}$ | 28 |
| 40 | Me | Et | —C$_3$H$_6$— | A (2-MePh) | 7.7 | — | 36 |
| 41 | Me | Me | —C$_3$H$_6$— | A (3-MePh) | 8.2 | — | 28 |
| 42 | Me | Me | —C$_3$H$_6$— | A (4-F-2-MePh) | 8.4 | — | 39 |
| 59 | Me | Me | —C$_3$H$_6$— | A (1-naphthyl) | 7.3 | — | — |
| 60 | Me | Me | —C$_3$H$_6$— | A (2-CF$_3$-Ph) | 7.2 | — | — |
| 61 | Me | Me | —C$_3$H$_6$— | A (2-cyclohexyl-Ph) | 7.6 | — | — |
| 62 | Me | Me | —C$_3$H$_6$— | A (2-allyl-Ph) | 7.4 | — | — |

TABLE 7-continued

Biological Test Data For Selected Formula XXI Compounds Wherein X = O

XXI $$\text{structure: } R^5O_2C\text{-pyridine with } NO_2\text{-phenyl, } CO_2\text{-Y-Z}$$

(Z = NHCH₂CH(OH)CH₂OAr (A) or —ArOCH₂CH(OH)CHNR⁷R⁸ (B))

| Ex. No. | $R^2$ | $R^5$ | Y | Z (Ar) | Calcium (pA₂)[a] | β-Binding (IC₅₀)[b] | Vasodilation[c] |
|---|---|---|---|---|---|---|---|
| 63 | Me | Me | —C₃H₆ | (tetralone) | 8.8 | — | — |
| 64 | Me | Me | —C₃H₆ | (decalindiol) | 7.3 | — | — |
| 65 | Me | Me | —C₃H₆ | (thiadiazole-morpholine) | — | — | — |

[a]Calcium blockade as determined in a rat dorsal aorta; figures tabulated are pA₂ values; pA₂ values represent the negative logarithm of the molar concentration of the antagonist which reduces the effect of a dose of agonist to that of half the dose, i.e. a dose ratio of 2. A compound is considered "active" in this screening test if the pA₂ value is 7 or greater.
[b]β-Receptor binding in animal heart tissue. Data listed are IC₅₀ values, with an IC₅₀ of <10⁻⁶ mM being considered as active. Reference compound data: Sotalol, 8 × 10⁻⁷; Practolol, 1 × 10⁻⁶; metoprolol, 5 × 10⁻⁷; nifedipine, >10⁻⁶.
[c]Vasodilation results given as % reduction in mean arterial blood pressure 30 minutes after dosing in the angiotensin-supported ganglion-blocked rat. A 20% or greater reduction in MABP at a dose of 1 mg/kg is considered "active".
[d]A dash (—) indicates that test results are not available.
[e]Vasodilation [as in c above] but at 10 mg/kg.
[f]Lethal at 1.0 mg/kg.

As can be seen by examination of the biological test data of Table 7; biological activities in one or more of the tests utilized (calcium ion blockade, β-binding, and vasodilation) indicate cardiovascular pharmacological properties which would make these compounds useful in treating cardiovascular disorders such as angina and hypertension. Given the number and variety of compounds tabulated in Table 7, it appears that these useful pharmacological properties are exhibited by the entire series of compounds embodied as Formula XXI.

What is claimed is:

1. A compound of Formula XXI

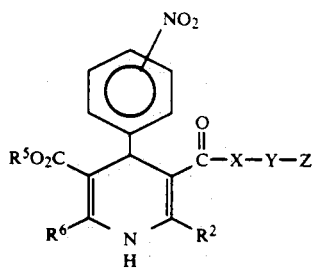

or the pharmaceutically acceptable acid addition salt thereof wherein $R^2$ is lower ($C_{1-4}$) alkyl, hydroxyalkyl, alkoxyalkyl, alkylaminoalkyl, dialkylaminoalkyl, phenyl or thienyl;

$R^5$ and $R^6$ are independently selected from lower alkyl, hydroxyalkyl, alkoxyalkyl, alkylaminoalkyl, or dialkylamino-alkyl and may be the same or different;

X is O;

Y is a covalent bond or a lower alkylene chain which may be substituted with a lower alkyl group, or is an alkyleneoxyalkylene, alkyleneaminoalkylene, alkylenecarboxamido, alkylenecarboxamidoalkylene, or alkylene thioureaalkylene chain; and Z is a beta-block moiety of Formula A or B

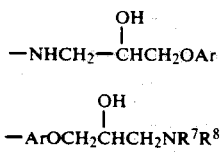

with Ar being naphthyl, 5,6,7,8-tetrahydronaphthyl either unsubstituted or substituted at one or more positions in the saturated ring with oxo or hydroxy groups, or phenyl either unsubstituted or optimally substituted at one or more ring positions with lower alkyl, alkoxy, alkoxyalkylene, ($C_{3-6}$)-cycloalkyl, allyl, aminocarbonylalkylene, cyano, halogen, hydroxyl, or trifluoromethyl, or Ar can be 4-(4-morpholino)-1,2,5-thiadiazol-3-yl; and $R^7$ and $R^8$ are independently chosen from lower alkyl and hydrogen.

2. The compound of claim 1 wherein Z is substructure A.

3. The compound of claim 2 in which Ar is 2-methylphenyl.

4. The compound of claim 1 wherein $R^4$ is 3-nitrophenyl.

5. The compound of claim 1, [2-[[3-(2-cyanophenoxy)-2-hydroxypropyl]amino]ethyl]3 methyl⁵2-ethyl-1,4-dihydro-6-methyl-4-(3-nitrophenyl)-3,5-pyridinedicarboxylate.

6. The compound of claim 1, [2-[[3-(2-cyanophenoxy)-2-hydroxypropyl]amino]-2,2-dimethylethyl]$^3$ methyl⁵ 2-ethyl-1,4-dihydro-6-methyl-4-(3-nitrophenyl)-3,5-pyridinedicarboxylate.

7. The compound of claim 1, [2-[[3-(2-cyanophenoxy)-2-hydroxypropyl]amino]-2,2-dimethylethyl]⁵ methyl³ 1,4-dihydro-2-methyl-6-(1-methylethyl)-4-(3-nitrophenyl)-3,5-pyridinedicarboxylate.

8. The compound of claim 1, [2-[[3-(2-methylphenoxy)-2hydroxypropyl]amino]-2,2-dimethylethyl]3 methyl15 2-ethyl-1,4-dihydro-6-methyl-4-(3-nitrophenyl)-3,5-pyridinedicarboxylate.

9. The compound of claim 1, [2-[[3-(2-bromophenoxy)-2-hydroxypropyl]amino]- 2,2-dimethylethyl]³ methyl⁵ 2-ethyl-1,4-dihydro-6-methyl-4-(3-nitrophenyl)-3,5-pyridinedicarboxylate.

10. The compound of claim 1, [2-[[3-(2-cyanophenoxy)-2-hydroxypropyl]amino]-2,2-dimethylethyl]³ methyl⁵ 1,4-dihydro-6-methyl-4-(3-nitrophenyl)-3,5-pyridinedicarboxylate.

11. The compound of claim 1, [3-[[3-(2-cyanophenoxy)-2-hydroxypropyl]amino]propyl]³ methyl⁵ 2-ethyl-1,4-dihydro-6-methyl-4-(3-nitrophenyl)-3,5-pyridinedicarboxylate.

12. The compound of claim 1, [2-[[3-(2-cyanophenoxy)-2-hydroxypropyl]amino]-2,2-dimethylethyl]⁵ methyl³ 1,4-dihydro-2-methyl-4-(3-nitrophenyl)-6-(2-thienyl)-3,5pyridinedicarboxylate.

13. The compound of claim 1, [2-[[3-[4-(2-methoxyethyl)-phenoxy[-2-hydroxypropyl]amino]-2,2-dimethylethyl]³ methyl⁵ 2-ethyl-1,4-dihydro-6-methyl-4-(3-nitrophenyl)-3,5-pyridinedicarboxylate.

14. The compound of claim 1, [2-[[3-(2-cyanophenoxy)-2-hydroxypropyl]amino]-2,2-dimethylethyl]methyl 1,4-dihydro-2,6-dimethyl-4-(3-nitrophenyl)-3,5-pyridinedicarboxylate.

15. The compound of claim 1, methyl [2-[[[[2-[[2-hydroxy-3-(2-methylphenoxy)propyl]amino]ethyl]amino]thiocarbonyl]amino]ethyl]1,4-dihydro-2,6-dimethyl-4-(3-nitrophenyl)-3,5-pyridinedicarboxylate.

16. The compound of claim 1, ethyl [2-[4-[3-2-hydroxy-(1-methylethyl)amino]propoxy]phenyl]ethyl]1,4-dihydro-2,6-dimethyl-4-(3-nitrophenyl)-3,5-pyridinedicarboxylate.

17. The compound of claim 1, ethyl [2-[4-[3-[(1,1-dimethylethyl)amino]-2-hydroxypropoxy]phenyl]ethyl]1,4-dihydro-2,6-dimethyl-4-(3-nitrophenyl)-3,5-pyridinedicarboxylate hydrochloride hemihydrate.

18. The compound of claim 1, ethyl [3-[[[4-[2-hydroxy-3-(1-methylethyl)amino]propoxy]phenyl]amino]carbonyl]propyl]1,4-dihydro-2,6-dimethyl-4-(3-nitrophenyl)-3,5-pyridinedicarboxylate.

19. The compound of claim 1, [3-[[3-(2-cyanophenoxy)-2-hydroxypropyl]amino]propyl]ethyl 1,4-dihydro-2,6-dimethyl-4-(3-nitrophenyl)-3,5-pyridinedicarboxylate.

20. The compound of claim 1, [2-[3-[4-(aminocarbonyl)methyl]
phenoxy]-2-hydroxypropyl]amino]-2,2-dimethylethyl]3 methyl15 2-ethyl-1,4-dihydro-6-methyl-4-(3-nitrophenyl)-3,5-pyridinedicarboxylate.

21. The compound of claim 1, [2-[[[[4-[2-hydroxy-3-[(1-methylethyl)amino]propoxy]phenyl]methyl]carbonyl]amino]-2,2-dimethylethyl]³ methyl⁵ 2-ethyl-1,4-dihydro-6-methyl-4-(3-nitrophenyl)-3,5-pyridinedicarboxylate.

22. The compound of claim 1, methyl [3-[[3-(2-methylphenoxy)-2-hydroxypropyl]amino]propyl]1,4-dihydro-2,6-dimethyl-4-(3-nitro-phenyl)-3,5-pyridinedicarboxylate.

23. The compound of claim 1, ethyl [3-[[3-(2-:sethyl-phenoxy)-2-hydroxypropyl]amino]propyl]1,4-dihydro-2,6-dimethyl-4-(3-nitro- phenyl)-3,5-pyridinedicarboxylate.

24. The compound of claim 1, methyl [3-[[2-hydroxy-3-(3-methylphenoxy)propyl]amino]propyl]1,4-dihydro-2,6-dimethyl-4-(3-nitrophenyl)-3,5-pyridinedicarboxylate.

25. The compound of claim 1, methyl [3-[[3-(4-fluoro-2-methylphenoxy)-2-hydroxypropyl]amino]propyl]1,4-dihydro-2,6-dimethyl-4-(3-nitrophenyl)-3,5-pyridinedicarboxylate.

26. The compound of claim 1, methyl [3-[[3-(1-naphthalenyloxy)2-hydroxypropyl]amino]propyl 1,4-dihydro-2,6-dimethyl-4-(3-nitrophenyl)-3,5-pyridinedicarboxylate.

27. The compound of claim 1, methyl [3-[[3-[2-trifluoromethyl)phenoxy]-2-hydroxypropyl]amino]propyl]1,4-dihydro-2,6-dimethyl-4-(3- nitrophenyl)-3,5-pyridinedicarboxylate.

28. The compound of claim 1, methyl [3-[[3-(2-cyclohexyl-phenoxy)-2-hydroxypropyl]amino]propyl]1,4-dihydro-2,6-dimethyl-4-(3-nitrophenyl)-3,5-pyridinedicarboxylate.

29. The compound of claim 1, [3-[[2-hydroxy-3-[2-(2-propenyl)phenoxy]propyl]amino]propyl]methyl 1,4-dihydro-2,6-dimethyl-4-(3-nitrophenyl)-3,5-pyridinedicarboxylate.

30. The compound of claim 1, [3-[[2-hydroxy-3-[(5,6,7,8-tetrahydro-5-oxo-1-naphthalenyloxy]propyl]amino]propyl]methyl 1,4-dihydro-2,6-dimethyl-4-(3-nitrophenyl)-3,5-pyridinedicarboxylate.

31. The compound of claim 1, methyl [3-[[3-(5,6,7,8-tetrahydro-6,7-cis-dihydroxy-1-naphthalenyloxy)-2-hydroxypropyl]amino]propyl]1,4-dihydro-2,6-dimethyl-4-(3-nitrophenyl)-3,5-pyridinedicarboxylate.

32. The compound of claim 1, [3-[[2-hydroxy-3-[[4-(4-morpholinyl)-1,2,5-thiadiazol-3-yl]oxy]propyl]amino]propyl]methyl 1,4-dihydro-2,6-dimethyl-4-(3-nitrophenyl)-3,5-pyridinedicarboxylate 33. A pharmaceutial composition for the treatment of hypertension comprising from about 5 to about 50 mg of a compound claimed in claim 1 in combination with a pharmaceutically acceptable, non-toxic inert carrier.

34. The antihypertensive method which comprises administering to a mammalian host having hypertension a non-toxic antihypertinsive effective dose of a compound claimed in claim 1.

* * * * *